（12）United States Patent
Stadelhofer

(10) Patent No.: US 8,734,392 B2
(45) Date of Patent: May 27, 2014

(54) DOSING DEVICE HAVING A PUMPING DEVICE

(75) Inventor: Peter Stadelhofer, Singen (DE)

(73) Assignee: Aptar Radolfzell GmbH, Radolfzell (DE)

( * ) Notice: Subject to any disclaimer, the term of this patent is extended or adjusted under 35 U.S.C. 154(b) by 2407 days.

(21) Appl. No.: 10/848,517

(22) Filed: May 18, 2004

(65) Prior Publication Data

US 2005/0015051 A1    Jan. 20, 2005

(30) Foreign Application Priority Data

May 20, 2003   (DE) .................................. 103 23 603

(51) Int. Cl.
*A61M 15/00*   (2006.01)
*A61M 11/00*   (2006.01)

(52) U.S. Cl.
CPC ........... *A61M 15/0065* (2013.01); *A61M 15/00* (2013.01); *A61M 2011/007* (2013.01)
USPC ..................... 604/124; 128/200.14

(58) Field of Classification Search
CPC .......................... A61M 15/00; A61M 15/0065; A61M 2011/007
USPC ............... 604/58, 123–124, 131; 128/200.14, 128/200.18, 200.21, 200.22, 200.15, 200.23
See application file for complete search history.

(56) References Cited

U.S. PATENT DOCUMENTS

| | | | |
|---|---|---|---|
| 905,087 A * | 11/1908 | Mallory | .................. 128/200.22 |
| 3,601,315 A | 8/1971 | Montalbo | |
| 3,856,185 A | 12/1974 | Riccio | |
| 3,907,206 A * | 9/1975 | Kondo | ........................... 239/357 |
| 4,067,499 A | 1/1978 | Cohen | |
| 5,366,122 A | 11/1994 | Guentert et al. | |
| 5,813,570 A | 9/1998 | Fuchs et al. | |
| 5,944,222 A | 8/1999 | Fuchs et al. | |
| 6,059,150 A | 5/2000 | Fuchs et al. | |
| 6,321,942 B1 | 11/2001 | Krampen et al. | |
| 6,367,641 B1 | 4/2002 | Garcia et al. | |
| 6,382,465 B1 | 5/2002 | Greiner-Perth | |
| 6,533,196 B1 | 3/2003 | Ouin et al. | |
| 2002/0082545 A1* | 6/2002 | Sennett et al. | .................. 604/32 |
| 2003/0005926 A1* | 1/2003 | Jones et al. | .............. 128/200.23 |

(Continued)

FOREIGN PATENT DOCUMENTS

| | | |
|---|---|---|
| DE | 26 44 321 | 4/1978 |
| EP | 0 641 604 A2 | 3/1995 |
| MX | 9909975 A | 4/2000 |
| WO | WO 9939992 A1 * | 8/1999 |

OTHER PUBLICATIONS

European Patent Office Search Report dated Dec. 16, 2005 (4 pages).

*Primary Examiner* — Nicholas Lucchesi
*Assistant Examiner* — Gerald Landry, II
(74) *Attorney, Agent, or Firm* — Flynn, Thiel, Boutell & Tanis, P.C.

(57) ABSTRACT

A dosing device having a pumping device delivering at least one medium into a pumping channel running along a pumping axis, as well as an applicator having at least one application opening is known.
According to the invention, the applicator has at least one flow channel linking the pumping channel with the application opening and which is oriented transversely to the pumping axis, while the application opening is positioned laterally on the applicator.
Use for pharmaceutical applications.

22 Claims, 11 Drawing Sheets

(56) References Cited

U.S. PATENT DOCUMENTS

Figure 1:
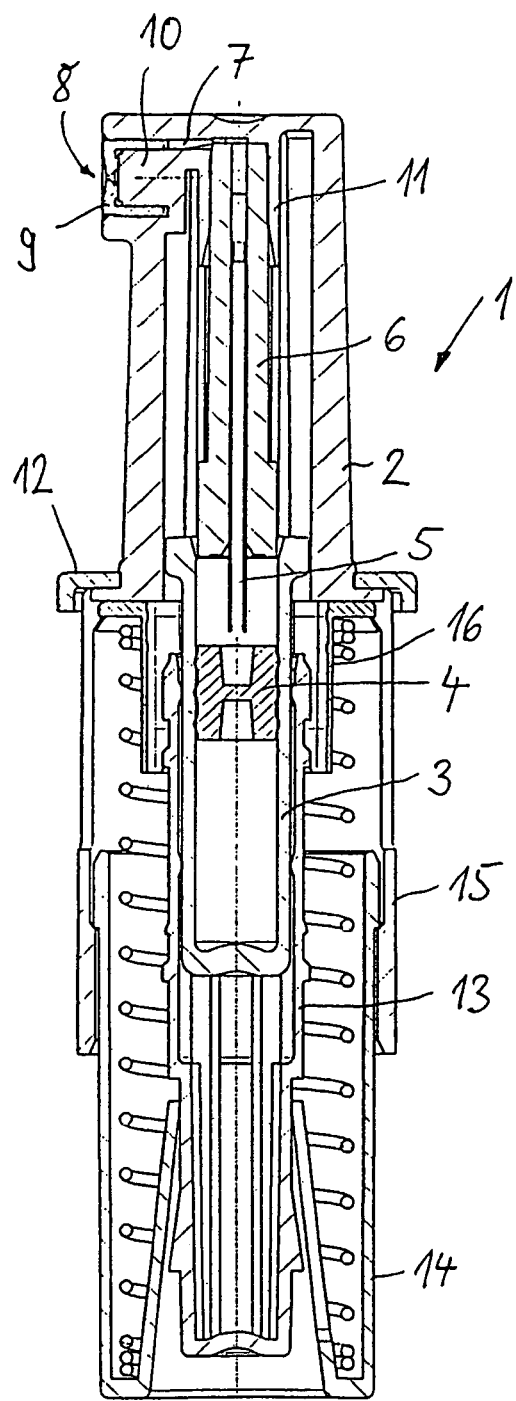

| | | | |
|---|---|---|---|
| 2003/0145849 A1* | 8/2003 | Drinan et al. | 128/200.14 |
| 2003/0164385 A1 | 9/2003 | Masuzzo et al. | |
| 2003/0209238 A1* | 11/2003 | Peters et al. | 128/200.14 |
| 2003/0209567 A1 | 11/2003 | Crosnier et al. | |
| 2007/0186927 A1* | 8/2007 | Djupesland et al. | 128/203.15 |

\* cited by examiner

DOSING DEVICE HAVING A PUMPING DEVICE

The invention relates to a dosing device provided with a pumping device, which delivers at least one medium into a pumping channel running along a pumping axis, as well as with an applicator having at least one application opening.

Such a dosing device is known from DE 197 00 437 A1. The known dosing device has a medium reservoir closed by means of a piston or plunger plug. An applicator is positioned in thrust-movable manner relative to the medium reservoir and relative to the piston plug. The applicator is constructed as a nose adaptor and has a finger rest or support to permit an actuation of the dosing device. The applicator contains a pumping channel, which terminates in a hollow needle towards the medium reservoir, said hollow needle being able to perforate the piston plug. As a result of the relative movement between applicator and medium reservoir, following the perforation of the piston plug, the latter is forced in the direction of the medium, so that the latter is compressed and delivered through the pumping channel to a nose adaptor application opening. The application opening is co-axial to the pumping axis on an outside of the nose adaptor.

The problem of the invention is to provide a dosing device of the aforementioned type particularly suitable for sublingual application.

This problem is solved in that the applicator has at least one flow channel linking the pumping channel with the application opening and which is oriented transversely to the pumping axis and in that the application opening is positioned laterally on the applicator. As a result of the solution according to the invention, starting from the pumping axis, the medium flow is deflected sideways and therefore at least substantially radially. The solution according to the invention is particularly suitable for a construction in which the pumping device is in the form of a thrust piston pump, which is operated manually. The pumping function corresponds to the dosing pump known from DE 197 00 437 A1. For an oral and in particular sublingual application, in simple manner the dosing device can be placed upright in front of a mouth of a person to be supplied. As a result of the laterally positioned application opening, on operating the pump in a roughly up-right position of the dosing device necessarily an application takes place into the mouth and preferably under the tongue. Preferably a liquid medium is applied. This is preferably introduced by atomization or dripping. In a particularly preferred construction an application axis of the application opening for the medium is oriented roughly parallel to the support or rest axes of the finger parts of the user resting on a finger rest of the applicator. It is alternatively possible to orient the application axis at right angles to the rest axes of two parallel fingers, preferably an index finger and a middle finger. However, in this embodiment it is obviously also possible to position the application opening laterally and therefore substantially radially to the applicator axis, i.e. pumping axis. The solution according to the invention is particularly suitable for pharmaceutical uses, but also for cosmetic and other uses.

According to a development of the invention, the at least one application opening is provided in an atomizing or spraying nozzle, which is located in the applicator in the flow channel outlet side. This makes it possible to atomize the at least one medium. As a function of the spraying nozzle construction different spraying characteristics can be achieved. The spraying nozzle can also be made adjustable, so as to be able to bring about variable spraying characteristics.

According to a further development of the invention, the spraying nozzle is integrally integrated into the applicator. Preferably the applicator is a plastic casing in which the spraying nozzle is shaped in one piece.

According to another development of the invention, the spraying nozzle is manufactured as a separate component and is joined to the applicator. In this embodiment, in the applicator, which is preferably in the form of a plastic component, a reception area is formed permitting an insertion or application, as well as a fixing of the spraying nozzle. For this purpose on the spraying nozzle and/or on or in the reception area of the applicator are formed in one piece corresponding guidance, securing or locking areas, so that for insertion, adjustment and fixing of the spraying nozzle no additional components are needed.

According to a further development of the invention with the flow channel is associated at least one flow guidance means, particularly a filler. Clearly defined applications are made possible through the flow guidance means. Thus, it is in particular possible as a result of the filler to create an annular space immediately upstream of a nozzle outlet and which produces a desired spraying characteristic in conjunction with a suitable nozzle geometry.

According to a further development of the invention, the flow guidance means is integrally integrated into the applicator. This construction is particularly advantageous if the applicator is a plastic component and the at least one flow guidance means is an integral part or portion of said plastic component. Advantageously a filler is provided, which is integrally integrated into the applicator.

According to another development of the invention, the flow guidance means is manufactured as a separate moulding and is inserted in the applicator. Preferably the flow guidance means is associated with the flow channel. In a preferred embodiment the flow guidance means is constituted by an at least substantially cylindrical filler, which is inserted in the applicator from one side coaxially to a longitudinal axis of the flow channel.

According to a further development of the invention, the cross-section of the application opening corresponds to the cross-section of the flow channel or is only slightly modified with respect thereto. Thus, a transition from the flow channel to the application opening takes place substantially without any change in the flow cross-section and therefore at least substantially without any additional flow guidance function. As a result of this construction an application by dripping or dropping is reliably possible.

According to a further development of the invention, with the applicator is associated a finger rest, positioned relative to an application axis of the application opening in such a way that when at least one finger part of a user resting on the finger rest is applied below a lower lip of the user there is a medium application into the users mouth. This is an ergonomically particularly favourable construction. The user more particularly places front joint parts of his index and middle finger resting on the finger rest and preferably flanking the applicator below the lower lip and therefore just above his chin. Advantageously the application axis, i.e. a main outlet axis of the application opening for the discharge of the medium is positioned roughly level with the mouth, so that with the mouth open necessarily medium is applied into the mouth. Alternatively, with the dosing device turned by 90ø, the user can apply said device to the lower lip. Then, preferably, only an index finger is applied to the face between chin and mouth together with the corresponding part of the finger rest, whereas the middle finger flanking the applicator on the opposite side and resting on the finger rest is spaced from the face. Although in this variant the application axis is also oriented radially to the pumping axis, it is at right angles to the finger rest axes of the finger resting on the finger rest. Obviously the right-angled orientation is chosen in such a way that the application axis is directed towards and not away from the mouth. This means that, starting from the pumping axis, the application axis projects radially in the direction in which the lateral rest surface for the index finger is formed on the finger rest. These two variants are implemented alternatively if the application axis passes parallel or at right angles to the finger rest axis of at least one finger part.

According to a further development of the invention, relative to the pumping axis, the application axis is oriented with an axial spacing with respect to the finger rest selected in such a way that on positioning the dosing device with finger rest located below the lower lip of the user, the application opening is oriented in the direction of and level with the open mouth of the user. This construction ensures that the axial spacing of the application axis from the finger rest is neither too great nor too small. This ensures that with a correct finger engagement below the lower lip there is indeed an application into the mouth.

According to a preferred embodiment, the applicator has a piston extension, in an unloaded rest position of the applicator in radially guided manner it at least partly axially projects into an open cylindrical portion of a medium reservoir. As a result of the radially guided, partial axial projection of a piston extension of the applicator into an open cylindrical portion of a medium reservoir when the applicator is in an unloaded rest position, it is ensured that independently of the intensity of a corresponding actuating movement, a reliable, centred perforation of the piston plug is ensured. Leaks and inadequate dosings of the dosing system are consequently reliably avoided.

Further advantages and features of the invention can be gathered from the following description of preferred embodiments of the invention, the attached claims and the drawings, wherein show:

FIG. 1 A sectional representation of a first embodiment of an inventive dosing device for multiple use.

Figure 2:
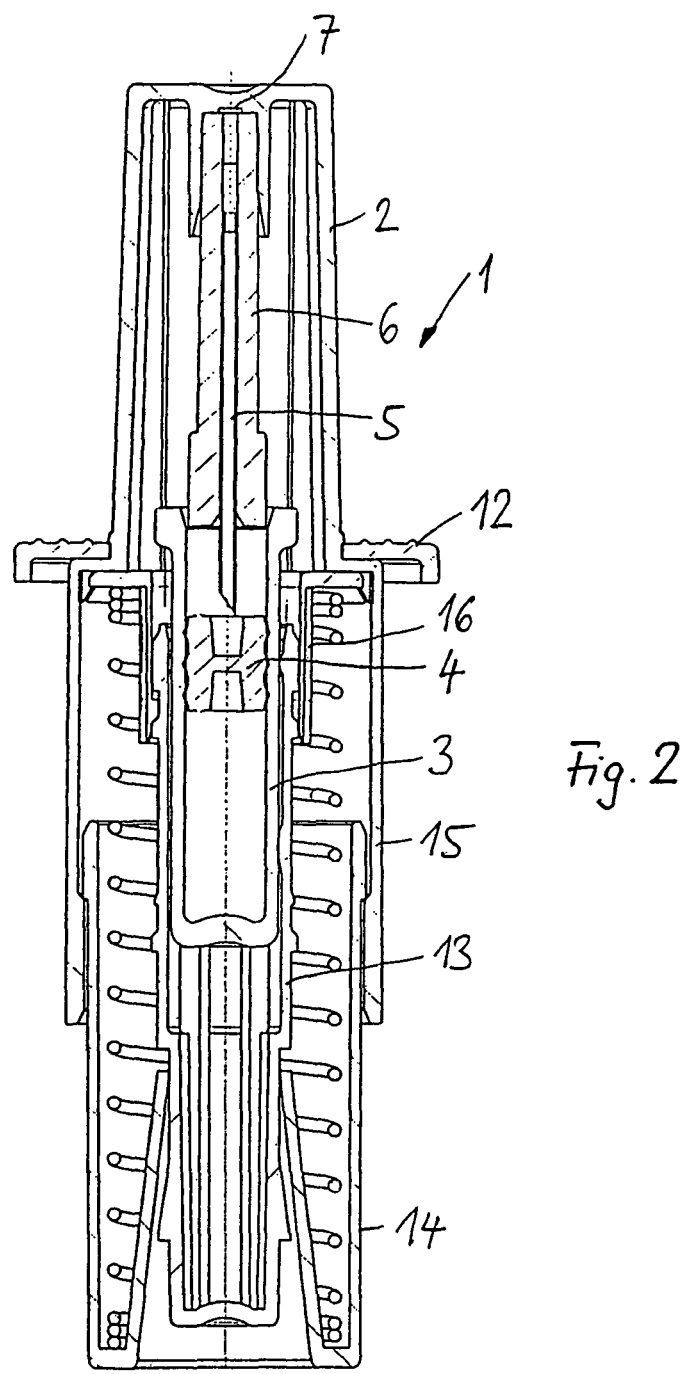

FIG. 2 A sectional representation of the dosing device according to FIG. 1 turned by 90ø relative to the median longitudinal axis of the dosing device of FIG. 1.

Figure 3:
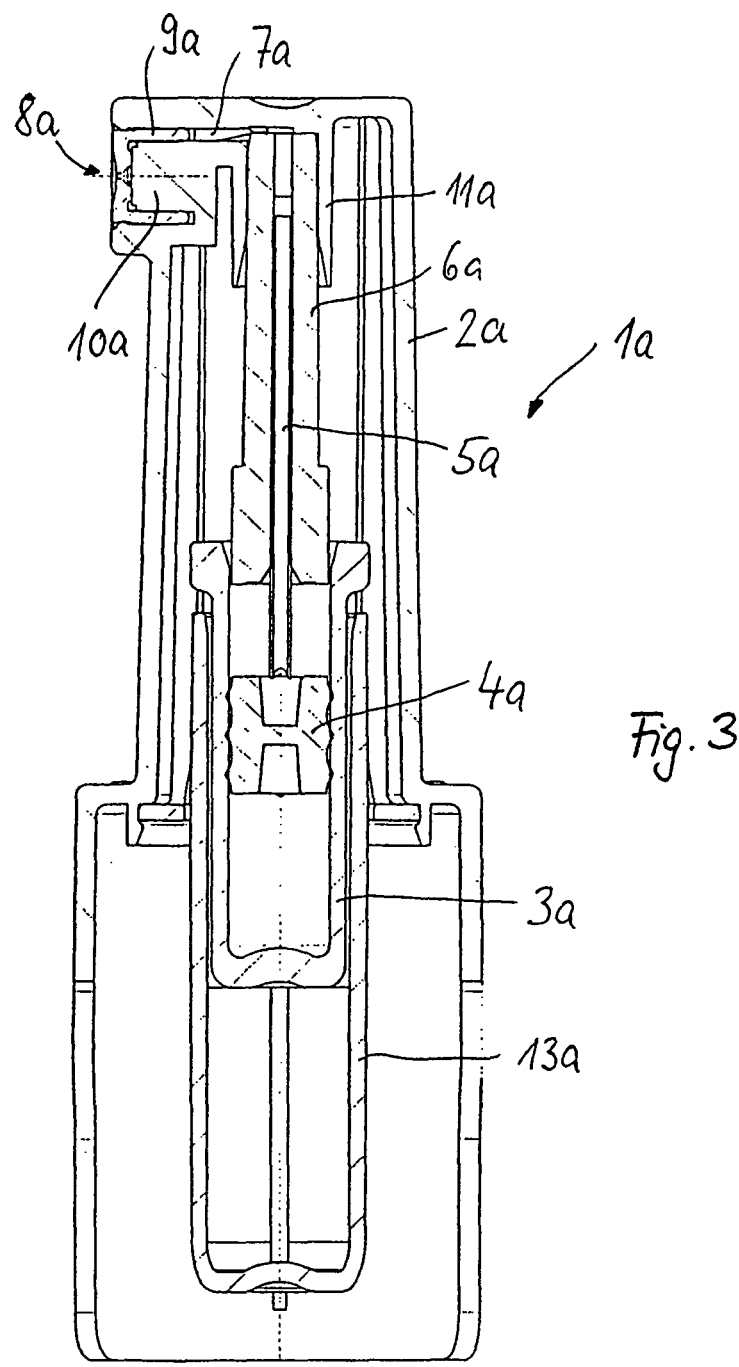

FIG. 3 A sectional representation of a further embodiment of a dosing device similar to FIG. 1.

Figure 4:
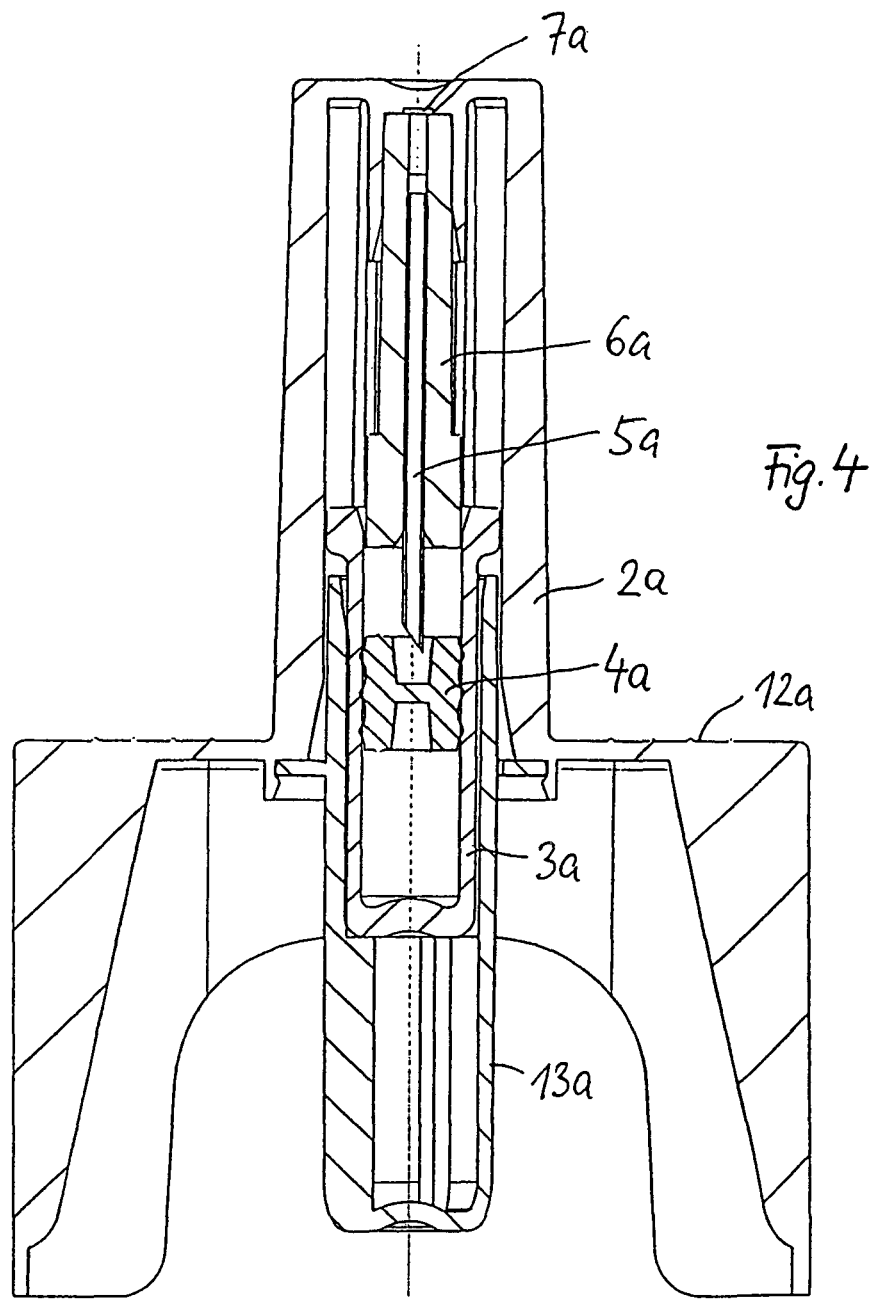

FIG. 4 A sectional view of the dosing device of FIG. 3 turned by 90ø.

Figure 5:
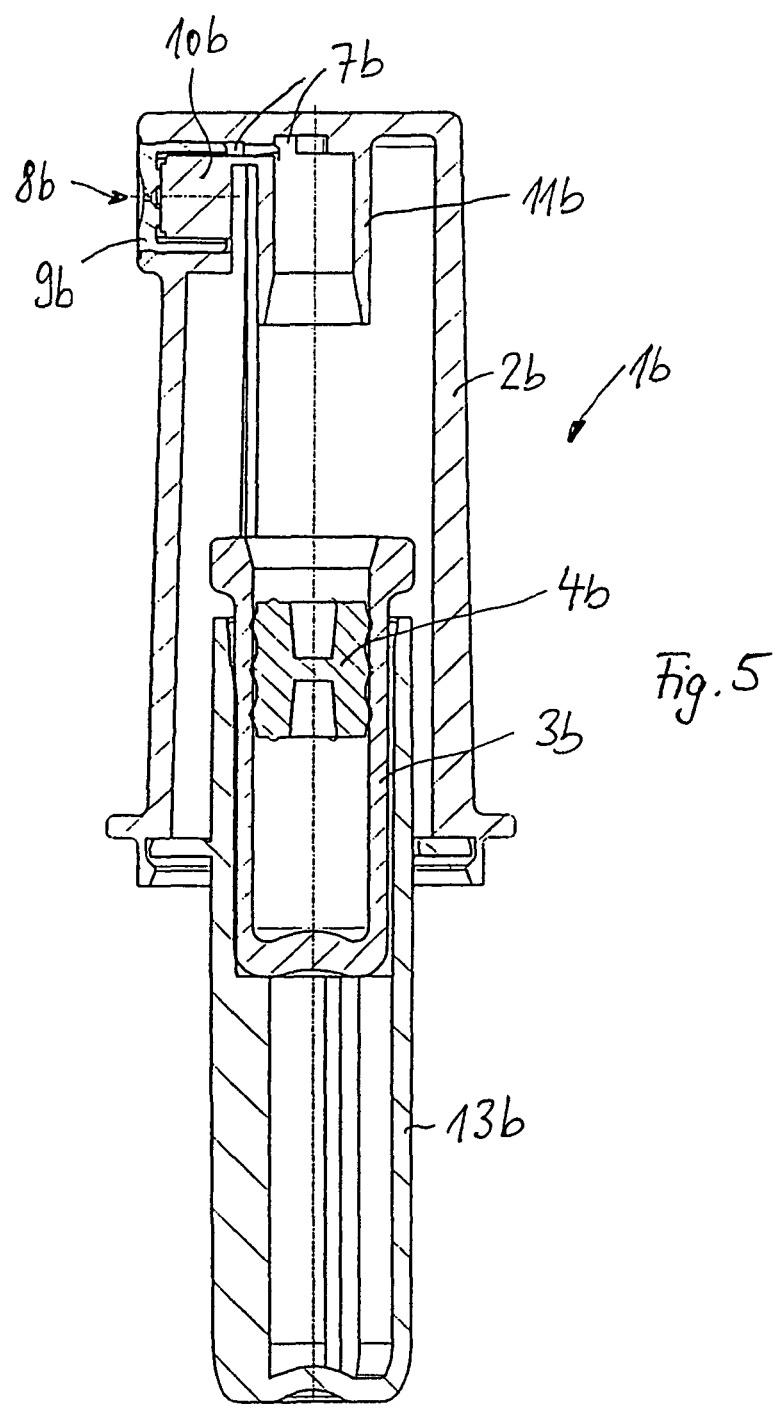

FIG. 5 A sectional representation of another embodiment of a dosing device similar to FIGS. 3 and 4.

Figure 6:
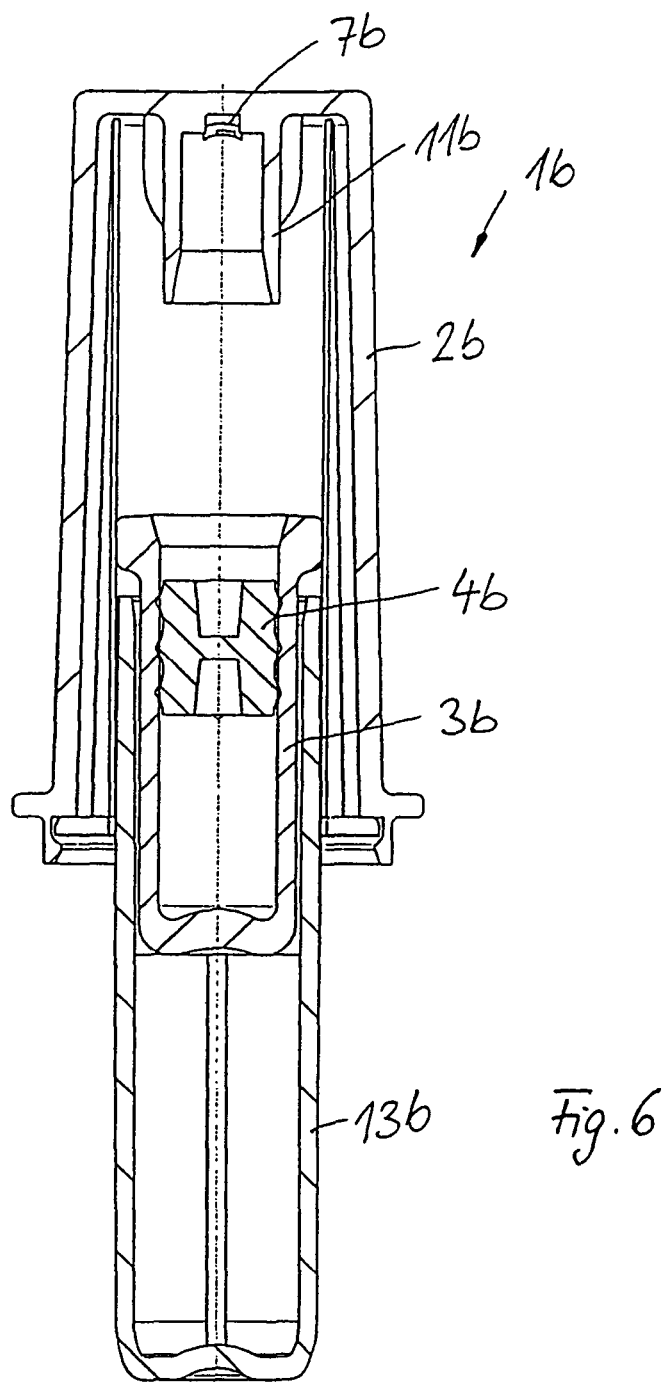

FIG. 6 The dosing device of FIG. 5 in a sectional representation turned by 90ø.

Figure 7:
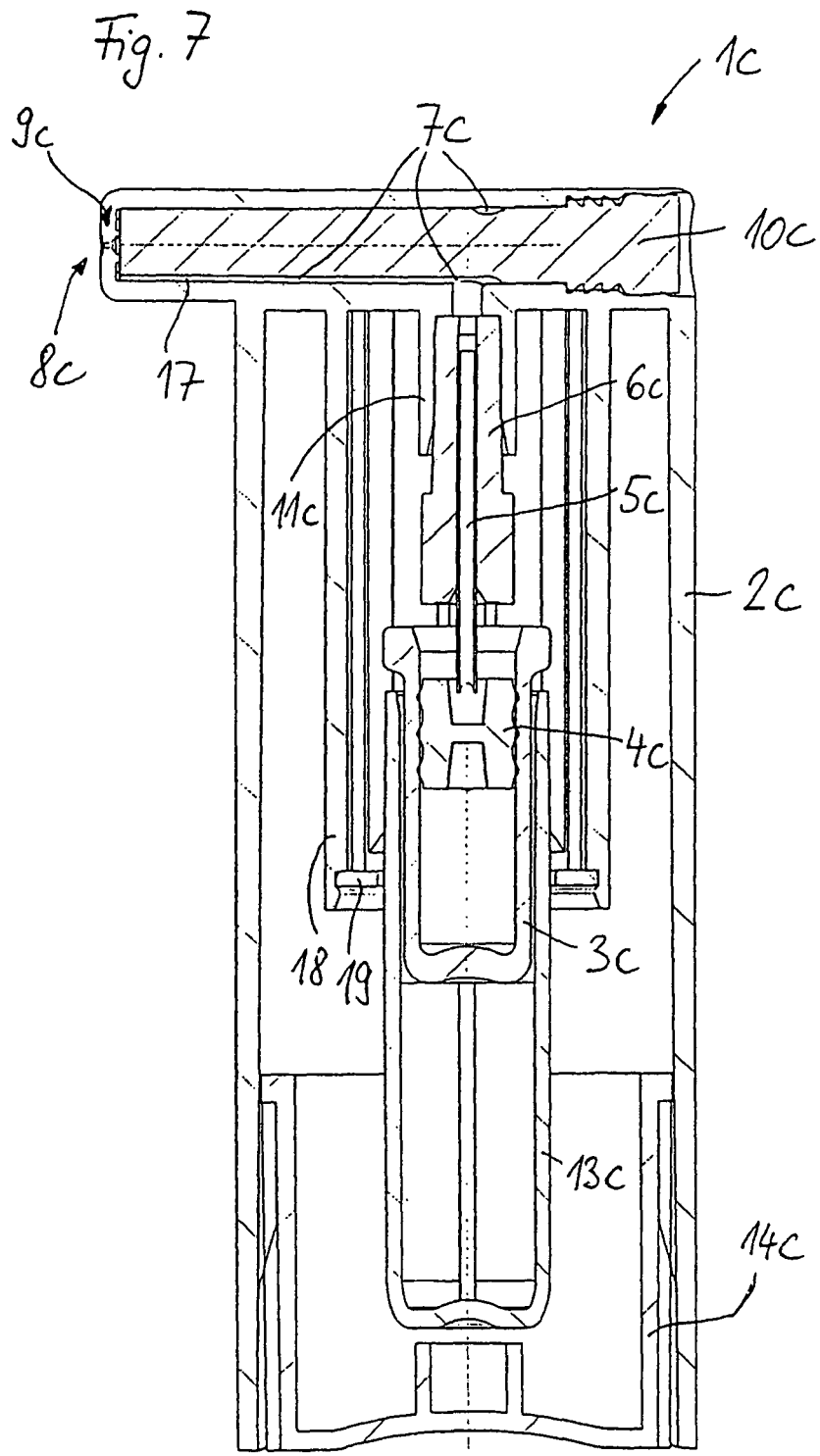

FIG. 7 Another embodiment of an inventive dosing device in a sectional representation.

Figure 8:
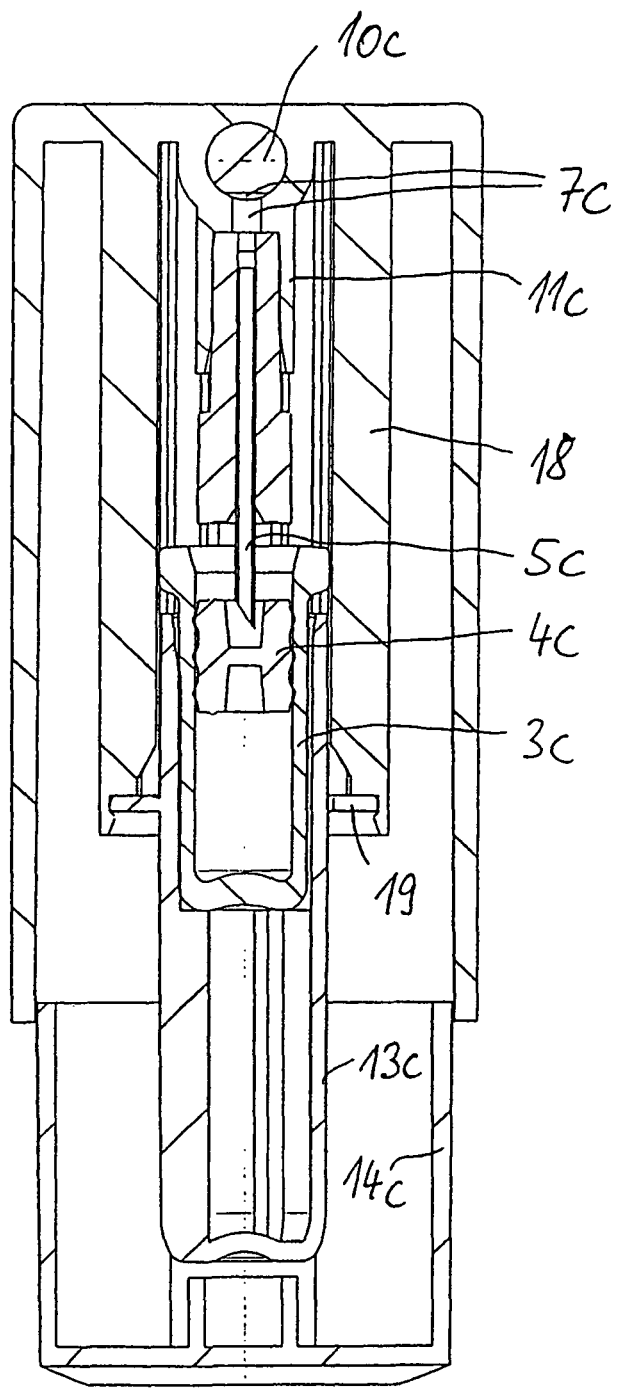

FIG. 8 The dosing device of FIG. 7 in a sectional representation turned by 90ø.

Figure 9:
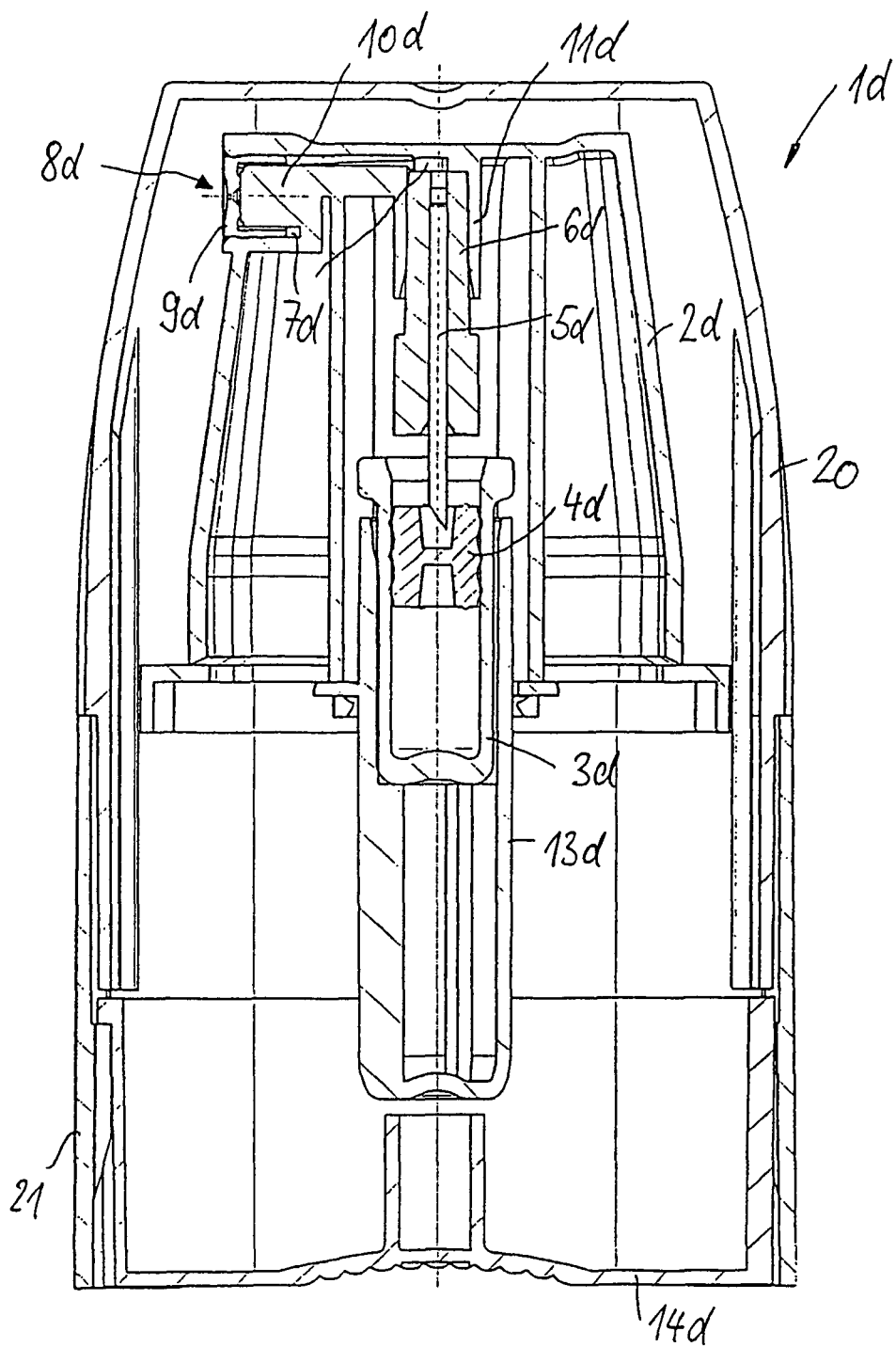

FIG. 9 Another embodiment of an inventive dosing device with protective cap in a sectional representation.

Figure 10:
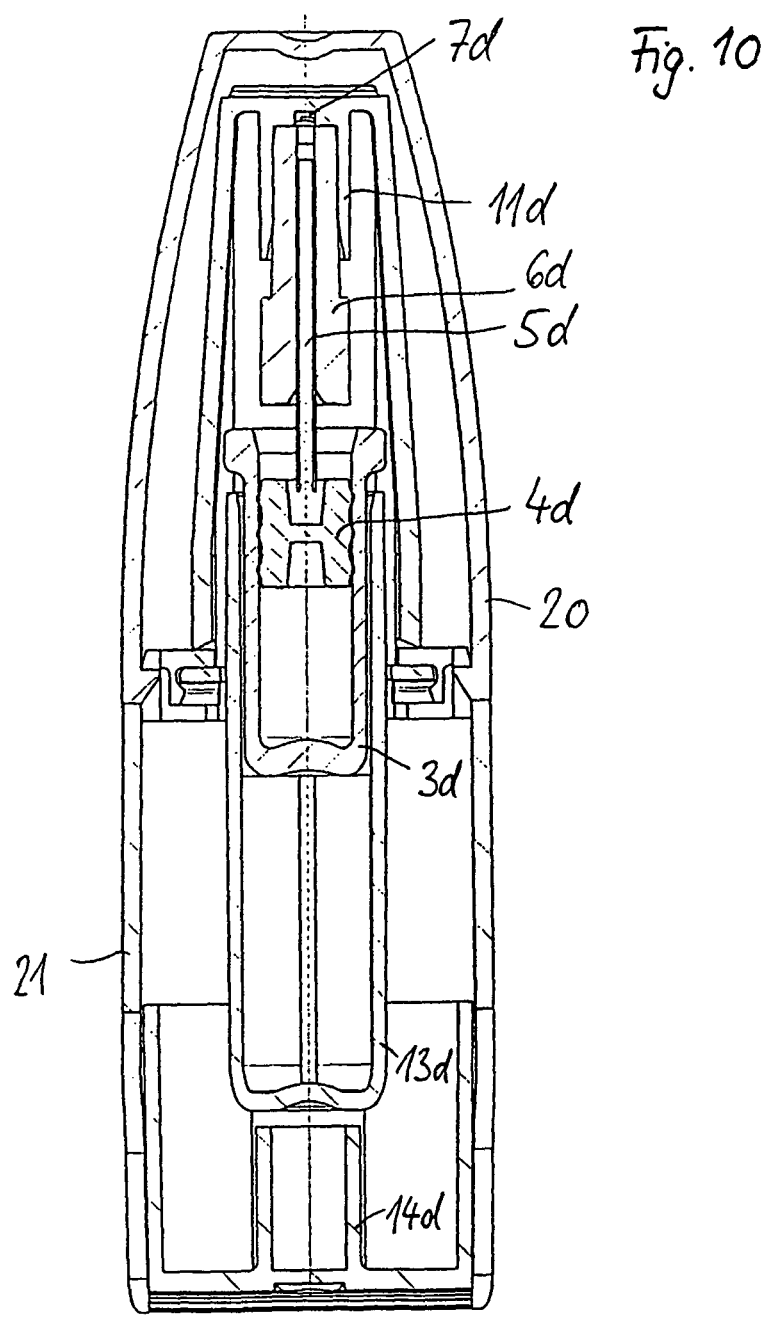

FIG. 10 The dosing device of FIG. 9 in a sectional view turned by 90ø.

Figure 11:
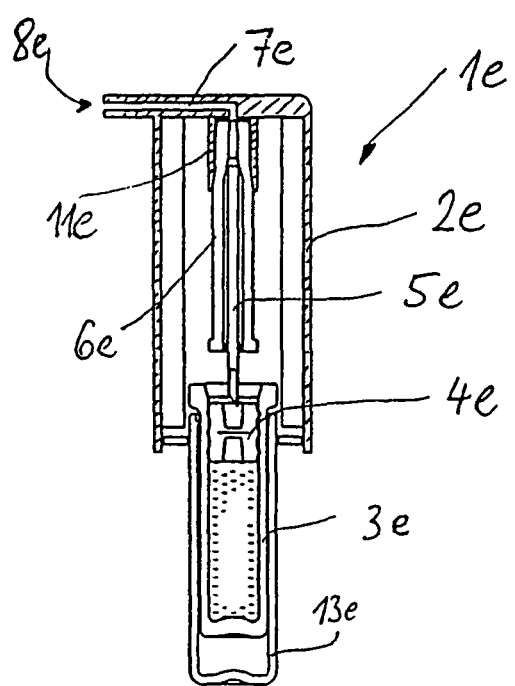

FIG. 11 A smaller scale view compared with FIGS. 1 to 10 of another embodiment of an inventive dosing device constructed for application by dripping.

The different embodiments of the dosing devices described hereinafter relative to FIGS. 1 to 11 are preferably intended for pharmaceutical applications and are designed for applying corresponding active agents by means of a liquid medium. In the embodiment shown the active agents are dissolved in the liquid medium. The solution according to the invention and the embodiments described hereinafter, with minor modifications, are also suitable for providing the active agents in the form of solids, particularly in powder form and to bring same into contact with a liquid carrier medium prior to a corresponding application process and to in this way dissolve the pulverulent active agents in the medium. The subsequent application corresponds to the embodiments described hereinafter. The embodiments shown in FIGS. 1 to 11 are constructed as single or double dosing devices. This means that the stored, liquid medium can be discharged in a single dosing process or two separate dosing processes. The single dosing device is consequently suitable for a single use and the double dosing device for a double use. All the dosing devices according to FIGS. 1 to 11 are intended for oral applications, particularly sublingual applications.

All the dosing devices according to FIGS. 1 to 11 are at least largely constructed from plastic parts produced by injection moulding processes. Only the subsequently further described hollow needles 5 to 5e are made in fundamentally known manner from metal in all the embodiments. The medium reservoir 3 to 3e is preferably made from glass. In the embodiment according to FIGS. 1 and 2 there is also a metal helical compression spring serving as a spring storage means or return spring and said spring is preferably made from spring steel. The dosing devices according to FIGS. 1 to 10 are shown on a larger scale in order to clearly reveal the details of the individual components of the dosing devices.

The dosing device according to FIGS. 1 and 2 has a pumping device in the form of a thrust piston pump. The dosing device 1 has a hollow cylindrical medium reservoir 3, which is open to a top side directed upwards in FIGS. 1 and 2. In the medium reservoir 3 is tightly, but displaceably positioned a piston plug 4, which is made from an elastic material, particularly an elastomer. In the space bounded by the medium reservoir 3 and piston plug 4 is provided a liquid medium having at least one pharmaceutical active agent. The medium reservoir 3 is received and bottom-supported in an actuating cylinder 13. The actuating cylinder 13 is surrounded by a sleeve-like actuating member 14, which is mounted in thrust-movable manner in a reception ring 15 along a pumping axis coaxially traversing the medium reservoir 3. The actuating cylinder 13 is held and displaceably mounted in a support sleeve 16. For the corresponding holding or fixing or stop functions on the different components are provided detents, stop shoulders and other profile sections, so that on actuating the dosing device 1 there is a time-displaced cooperation between the components. The dosing device 1 according to FIGS. 1 and 2 is intended for double dosing.

The reception ring 15 is part of an applicator 2, to which is detachably fixed as a separate component a finger rest 12. The applicator 2 has a sleeve or bell-like construction and is provided in its interior with not shown guide grooves running axially parallel to the pumping axis and in which is positioned an upper marginal area of the medium reservoir 3, so as to ensure an axial displaceability of the applicator 2 relative to the medium reservoir 3. In its interior and in the vicinity of the top side thereof, the applicator 2 has a reception sleeve 11 shaped on in one piece and which projects downwards coaxially to the pumping axis. A substantially cylindrical piston part 16 is axially inserted in the reception sleeve 11 and in the same is formed a pumping channel running coaxially to the pumping axis. The hollow needle 5 is coaxially inserted in the pumping channel and the tip of the hollow needle 5 projects downwards out of the piston part 6. On actuating the dosing device 1, the tip of the hollow needle 5 perforates the piston plug 4. In the upper frontal area the pumping channel passes into a flow channel 7 oriented at right angles and therefore radially to the pumping axis and which issues into a spraying nozzle 9 having a nozzle outlet 8 acting as the outlet opening. The flow channel 7 is constructed in one piece in the applicator 2 and continues towards the nozzle outlet 8 into an annular space open to the side of the applicator 2. The annular space is formed by a cylindrical filler shaped in one piece in the applicator 2 and which is directed outwards radially to the pumping axis. The annular space open to the side of the applicator 2 is closed by a nozzle insert, which forms the spraying nozzle 9. The nozzle outlet 8 shaped in one piece into the nozzle insert, which is made from plastic. In simple manner and radially to the pumping axis, the nozzle insert is inserted from the outside in the annular space and is detachably or undetachably fixed there by suitable means. Fixing can take place positively, non-positively or integrally. A main spraying direction of the spraying nozzle 9 is brought about by the axis of symmetry of the filler 10 and is consequently oriented transversely to the pumping axis, i.e. radially to the pumping axis. Considered circumferentially, the spraying axis position is such that it is roughly parallel to imaginary rest or support axes for fingers resting on the finger rest 12. If, according to FIG. 2, an index finger and a middle finger rest on both sides of applicator 2 on finger rest 12, then the two fingers are oriented roughly parallel to one another and flank the applicator 2 from both sides. The spraying nozzle 9 is also oriented roughly parallel to the finger orientation, so that the spraying axis is roughly parallel to the orientation of the finger parts resting on the finger rest 12. The dosing device 1 is preferably gripped in such a way that the flow channel and therefore the annular space of the applicator 2 open in the direction of the fingertips. A user is now able to apply below his lower lip the fingertips of the index and middle fingers resting on the finger rest 12, so that the spraying nozzle 9 necessarily projects towards the open mouth. This permits an ergonomically favourable, oral and in particular sublingual application.

The operating principle of the dosing device 1a according to FIGS. 3 and 4 essentially corresponds to that of the dosing device 1 described relative to FIGS. 1 and 2. Here again a thrust piston pump constitutes the pumping device. The essential difference of the dosing device 1a is firstly that it is only intended for a single use and secondly on the applicator 2a the finger rest 12a is also shaped in one piece. The actuating member 13a receiving the medium reservoir 3 is so constructed that it can be pressed upwards from below and in a direct manner by a user's thumb. In fundamentally known manner the actuating member 13a is held by locking webs which break away when pressure is applied by a thumb and allow a corresponding thrust movement. Also in the embodiment according to FIGS. 3 and 4 a spraying axis of the nozzle outlet 8a of spraying nozzle 9a is oriented transversely and radially to the pumping axis in such a way that it is parallel to the imaginary rest axes of the corresponding finger parts of the index and middle fingers. This gives rise to the same advantages and application functions as in the embodiment according to FIGS. 1 and 2. Constructionally and functionally identical parts are given the same reference numerals as in the embodiment according to FIGS. 1 and 2, but the letter a is added thereto. FIG. 3 reveals that the sleeve-like nozzle insert of spraying nozzle 9a is positively held in the applicator 2a in the inserted state, because a front marginal region of the annular space formed in the applicator 2a is provided with undercuts projecting slightly into said space. In addition, it is possible to see the design of the nozzle insert 9a. In a front area of the filler 10a between the latter and the nozzle insert 9a is formed a circumferential annular clearance which is open to the centrally oriented nozzle outlet 8a. The flow channel 7a is connected to the annular clearance in not shown manner by means of corresponding flow channel portions, which cannot be seen in FIGS. 3 and 4. The flow channel 7a branches away from the pumping channel above the filler 10a, so that the liquid medium is brought to the annular space in an upper area of the latter.

Both in the embodiment according to FIGS. 1 and 2 and in that according to FIGS. 3 and 4, from the axial length of the piston part 6, 6a related to a pump axis it is designed in such a way that in the unloaded rest position of the applicator, as shown in FIGS. 1 to 4, it projects at least zonally and axially into the open front side of the medium reservoir 3, 3a. Preferably, the projecting in portion of the piston part 6, 6a has a cross-section chosen so that in said rest position it is oriented in the medium reservoir 3a substantially clearance-free and centred to a central longitudinal axis thereof (FIG. 3). In an upper front edge area the medium reservoir 3, 3a has a conically tapering centring opening in order to make it possible to bring about a further improved centring of the piston part 6, 6a on assembling the dosing device.

In the embodiment according to FIGS. 5 and 6 the dosing device 1b is only incompletely shown. In particular, the piston part and inserted hollow needle are not shown. As regards construction and design applicator 2b substantially corresponds to the previously described applicators 2 and 2a. The dosing device 1b is constructed in disposable form and the incompletely shown pumping device is designed as a thrust piston pump as in the embodiment of FIGS. 3 and 4. The reception sleeve 11b in which the piston part 6 is inserted also corresponds to the embodiment of FIGS. 3 and 4. The same applies with regards to the position of the flow channel 7b, the one-piece shaping of the filler 10b, the nozzle insert of atomizing nozzle 9b introduced from the radial outside and fixed in an annular space of the flow channel 7b and applicator 2b and the central position of the nozzle outlet 8b. Thus, for the disclosure of this embodiment supplementary reference can be made to the disclosure of the embodiments according to FIGS. 1 to 4. Constructionally and functionally identical components are given the same reference numerals as in the embodiments according to FIGS. 1 to 4, but accompanied by the addition of the letter b.

In the embodiment according to FIGS. 7 and 8 the dosing device 1c has a pumping device, which is constructed as a thrust piston pump corresponding to the dosing devices 1a and 1b according to FIGS. 3 to 6. Constructionally identical parts of the thrust piston pump are given the same reference numerals, accompanied by the addition of the letter c. The essential difference in the embodiment according to FIGS. 7 and 8 is that a filler 10c associated with the flow channel 7c is inserted from the outside and as a separate component in applicator 2c. The flow channel 7c has a flow axis extending transversely to the pumping axis of the thrust piston pump 3c to 6c, 13c, 14c. In addition, a nozzle outlet 8c of a subsequently further described atomizing nozzle is integrated integrally into a wall of the applicator 2c, in that during the manufacture of the plastic component of the applicator 2c, the nozzle outlet 8c and corresponding guide profilings, which serve as flow guidance surfaces for an atomizing function, are also shaped in. The flow channel 7c is roughly cylindrical and extends in an upper area of the applicator 2c radially the pumping axis. The nozzle outlet 8c is constructed in the vicinity of a nose extension projecting transversely to the pumping axis and which projects to the outside transversely to a wall of the applicator 2c. Obviously the nose extension is also an integral component of the applicator 2c. The cylindrical space formed by the flow channel 7c is widened to the nozzle outlet 8*c* and is open to said said opposite side. By means of the open side it is possible to insert the substantially cylindrical filler 10*c* into the cylindrical space forming the flow channel 7*c*. In its end region remote from the nozzle outlet 8*c*, the filler 10*c* has several circumferential sealing lips in the vicinity of a sealing head in order to reliably fix the filler 10*c* in the applicator 2*c* and also reliably seal the flow channel 7*c* with respect to the side facing the nozzle outlet 8*c*. The substantially cylindrical filler 10*c* has a diameter which at least largely corresponds to the diameter of the flow channel 7*c*, in order to ensure a clearance-free positioning of the filler 10*c* in said flow channel 7*c*. Either the filler 10*c* or the flow channel 7*c* have one or more longitudinal profiling, which define slot or channel-like flow guidance sections 17. Thus, the medium is guided by flow channel portions defined by at least one longitudinal profiling and running between the outer contour of the filler 10*c* and an inner wall of the flow channel 7*c* to annular flow guidance sections on an inner wall of a front side of the nose extension into which issues the at least one flow guidance section 17. The annular flow guidance portions also define a flow path to the central nozzle outlet 8*c*. As in the previously described embodiments, the nozzle outlet 8*c* is chosen in such a way that in conjunction with the flow guidance means formed by a corresponding filler 10 to 10*c* and optionally additional flow guidance profilings, a desired atomizing function is obtained. Roughly in the axial extension of the pumping channel an annular groove is formed in the filler 10*c* and defines the start of the flow channel section 17, considered in the flow direction.

In the embodiment according to FIGS. 7 and 8 in the interior of the applicator 2*c* is also formed a circumferential area 18, which coaxially embraces the thrust piston pump and defines in its lower front end region a locking receptacle for a ring-like locking web 19, which when pressure is applied to the thrust piston pump tears away and therefore frees the path for an atomizing process. The dosing device 1*c* according to FIGS. 7 and 8 is also constructed for single dosing.

The pumping and atomizing function, as well as the structure of the associated parts of the dosing device 1*d* according to FIGS. 9 and 10 correspond to the embodiments previously described relative to FIGS. 3 to 6. Constructionally and functionally identical parts are given the same reference numerals, accompanied by the addition of the letter d. With regards to these constructionally and functionally identical parts reference is made to the disclosure of the earlier embodiments. The essential difference of the dosing device 1*d* is that it is additionally provided with a protective casing 20, 21. The protective casing 20, 21 comprises a protective cap 20 and a lower part 21, each made from plastic. The protective cap 20 and lower part 21 are so constructed and matched to the applicator 2*d* that actuation protection is provided without removing the cap 20. This means that the dosing device 1*d* cannot be actuated until the cap 20 is removed. This secures the dosing device 1*d* against unauthorized use, particularly by children. The protective cap 20 is locked on corresponding holding webs of the applicator 2*d* by means of not shown detents. As a result of an at least minor elastic deformability of the protective cap 20 it is possible to release the locking effect and remove the cap 20. It is now possible to operate the dosing device 1*d* as in the previously described embodiments. The dosing device 1*d* is also intended for single dosing.

In the dosing device 1*e* a pumping device is provided, which in the form of a thrust piston pump is constructed in accordance with the previously described embodiments. The essential difference of the present embodiment is that the applicator 2*e* is provided with an application opening 8*e* bringing about a dripping function. For this purpose in an upper front region of the applicator 2*e*, the casing defining the latter is extended outwards to the side and therefore transversely to the pumping axis by means of a nose-like lateral extension. Into said upper front area is shaped a flow channel 7*e* which, starting from the central pumping channel, leads to the outside and up to the application opening 8*e* and radially with respect to the pumping axis. Over its entire length the flow channel 7*e* has the same cross-section. The application opening 8*e* also has a cross-section corresponding to that of the flow channel 7*e*. This design makes it possible to apply dropwise the medium from the medium reservoir 3*e*. Dropwise application takes place in an easy way by constant, manually pressurizing the application cylinder 13*e*. For oral application the lateral extension of the applicator 2*e* provided with the application opening 8*e* is preferably oriented relative to the open mouth in such a way that the passing out drops enter the mouth and preferably go under the tongue.

The invention claimed is:

1. Dosing device having a pumping device, which delivers a medium into a pumping channel running along a pumping axis, and an applicator having at least one application opening, wherein the applicator has at least one flow channel having an outlet side at the application opening and an inlet side joined to the pumping channel, the flow channel being essentially linear between the inlet and outlet sides and being oriented transversely to the pumping channel and to the pumping axis, and wherein the application opening is positioned laterally on the applicator, and wherein a finger rest is associated with the applicator, and the pumping device includes an actuator having an outwardly projecting end that is movable relative to the finger rest, wherein the finger rest and the end of the actuator are so positioned relative to an application axis of the application opening that when at least one finger part of a user resting on the finger rest and another finger of a user located at the end of the actuator are applied below a lower lip of the user, medium can be applied to the mouth of the user.

2. Dosing device according to claim 1, wherein the at least one application opening is provided in a spraying nozzle, which is located in the applicator on the outlet side of the flow channel.

3. Dosing device according to claim 2, wherein the spraying nozzle is integrated into the applicator.

4. Dosing device according to claim 2, wherein the spraying nozzle is manufactured as a separate component and joined to the applicator.

5. Dosing device according to claim 1, wherein a filler is associated with the flow channel.

6. Dosing device according to claim 5, wherein the filler comprises a cylindrical filler integrated into the applicator.

7. Dosing device according to claim 5, wherein the filler is manufactured as a separate moulding and is inserted in the application opening and in the flow channel of the applicator.

8. Dosing device according to claim 1, wherein the cross-section of the application opening corresponds to or is only slightly modified compared with the cross-section of the flow channel.

9. Dosing device according to claim 1, wherein the application axis is parallel or at right angles to a finger rest axis of at least one finger part and the application axis is parallel to a flow channel axis of the at least one flow channel.

10. Dosing device according to claim 1, wherein the application axis is oriented radially outwardly and transverse to the pumping axis and in an axially spaced manner with respect to the finger rest, and is located so that on positioning the dosing device with the finger rest and the end of the actuator below the lower lip of the user, the application opening is oriented in the direction of and level with the open mouth of the user.

11. Dosing device according to claim 1, wherein the applicator includes a piston extension with the pumping channel formed therein, which in an unloaded rest position of the applicator in a radially guided manner projects at least partly and axially into an open cylindrical section of a medium reservoir.

12. Dosing device according to claim 11, including a piston plug sealing the medium reservoir.

13. Dosing device according to claim 12, including a hollow needle coaxially disposed in the pumping channel of the piston extension with a projecting tip for puncturing said piston plug to enable medium to enter the pumping channel when the actuator and the medium reservoir move toward the applicator.

14. Dosing device according to claim 1, wherein the dosing device is capable of providing only a single dose of the medium, the dosing device comprising a disposable dosing device.

15. Dosing device according to claim 1, wherein the dosing device is free from springs.

16. Dosing device according to claim 1, wherein the pumping channel and the flow channel together define a flow path for medium, the pumping channel is essentially linear, and the inlet side of the flow channel is joined to a first end of the pumping channel and the pumping channel has a second end associated with a medium reservoir, and wherein the joining of the flow channel to the first end of the pumping channel is the sole directional change in the flow path between the outlet side of the flow channel at the application opening and the second end of the pumping channel.

17. Dosing device for delivering a medium to a mouth of a user, comprising:
an elongate applicator having an open end and a closed end, the applicator adjacent the closed end forming at least one radially oriented flow channel having an outlet side associated with a radially oriented application opening and an inlet side, the flow channel being essentially linear between the inlet and outlet sides;
an elongate piston part disposed within the applicator and defining a pump channel having a pump axis oriented transversely to the at least one essentially linear flow channel of the elongate applicator, an end of the pump channel joining the inlet side of the flow channel to enable flow of medium therebetween;
a medium reservoir storing a medium;
an elongate actuator having an open end for receiving the medium reservoir and having a generally closed end, at least a portion of the medium reservoir and a portion of the actuator being disposed within the applicator at the open end thereof; and
a finger rest disposed about the applicator adjacent the open end thereof, the finger rest being so positioned relative to the application opening that when at least one finger part of a user resting on the finger rest is applied below a lower lip of the user, medium can be applied to the mouth of the user.

18. Dosing device according to claim 17, comprising a piston plug disposed at an open end of the medium reservoir to seal the medium reservoir before use thereof, the dosing device further comprising a hollow needle mounted in the pump channel of the piston part, wherein movement of the actuator toward the applicator causes the needle to puncture the piston plug to transfer the medium through the pump channel and the flow channel to the application opening.

19. Dosing device according to claim 17, wherein the actuator including the open end comprises an actuating cylinder having the open end receiving the medium reservoir and wherein a portion of the actuating cylinder is disposed within the applicator.

20. Dosing device according to claim 19, including a spraying nozzle that is secured in the application opening, the spraying nozzle including a nozzle outlet, and wherein the actuating cylinder includes locking webs that break away when pressure is applied to move the actuating cylinder toward the applicator so that the dosing device only provides a single dose of the medium, the dosing device comprising a single use disposable dosing device.

21. Dosing device according to claim 17, the actuator including the open end comprising an actuating cylinder having the open end receiving the medium reservoir and the actuator further comprising a sleeve-like actuating member configured to move the actuating cylinder toward the closed end of the applicator to apply the medium through the pump channel, the flow channel and the application opening to the mouth of the user.

22. Dosing device according to claim 17 wherein the pump channel is essentially linear, and the joining of the inlet side of the at least one flow channel and the end of the essentially linear pump channel provides the sole directional change in the flow path between the outlet side of the flow channel at the application opening and a second end of the pump channel.

* * * * *